US011191433B2

(12) United States Patent
Brancaccio et al.

(10) Patent No.: US 11,191,433 B2
(45) Date of Patent: Dec. 7, 2021

(54) APPARATUS AND METHOD FOR A PERSONALIZED REMINDER WITH INTELLIGENT SELF-MONITORING

(71) Applicant: Revibe Technologies, Inc., Wake Forest, NC (US)

(72) Inventors: Richard Brancaccio, Wake Forest, NC (US); Gwendolyn Campbell, Raleigh, NC (US); Christopher Guidry, Chapel Hill, NC (US)

( * ) Notice: Subject to any disclaimer, the term of this patent is extended or adjusted under 35 U.S.C. 154(b) by 0 days.

(21) Appl. No.: 15/898,492

(22) Filed: Feb. 17, 2018

(65) Prior Publication Data

US 2019/0254522 A1  Aug. 22, 2019

(51) Int. Cl.
| | | |
|---|---|---|
| A61B 5/00 | (2006.01) | |
| G09B 19/00 | (2006.01) | |
| G06F 1/16 | (2006.01) | |
| G06F 9/451 | (2018.01) | |
| G16H 20/30 | (2018.01) | |
| A61B 5/11 | (2006.01) | |

(52) U.S. Cl.
CPC .......... *A61B 5/0024* (2013.01); *A61B 5/1118* (2013.01); *A61B 5/486* (2013.01); *G06F 1/163* (2013.01); *G06F 9/453* (2018.02); *G09B 19/00* (2013.01); *G09B 19/0007* (2013.01); *G16H 20/30* (2018.01)

(58) Field of Classification Search
CPC ...... A61B 5/0024; G16H 20/30; G06F 9/453; G06F 1/163; G09B 19/0007
See application file for complete search history.

(56) References Cited

U.S. PATENT DOCUMENTS

| | | | |
|---|---|---|---|
| 5,402,108 A | 3/1995 | Tabin et al. | |
| 5,954,630 A | 9/1999 | Masaki et al. | |
| 6,461,316 B1 | 10/2002 | Lee et al. | |
| 6,558,165 B1 | 5/2003 | Curry et al. | |
| 9,529,385 B2 * | 12/2016 | Connor | G09B 19/0092 |
| 10,181,251 B2 * | 1/2019 | Gao | G06F 3/01 |
| 2004/0115603 A1 | 6/2004 | Reynolds | |
| 2007/0049788 A1 | 3/2007 | Kalinowski et al. | |
| 2007/0284401 A1 | 12/2007 | Hilliard | |
| 2008/0288023 A1 * | 11/2008 | John | A61N 1/37247 607/59 |
| 2011/0128151 A1 * | 6/2011 | Asad | A61B 5/1118 340/573.1 |
| 2012/0244503 A1 * | 9/2012 | Neveldine | G09B 19/00 434/236 |
| 2013/0110895 A1 | 5/2013 | Valentino et al. | |

(Continued)

FOREIGN PATENT DOCUMENTS

| | | |
|---|---|---|
| CA | 2039671 A1 | 10/1991 |
| DE | 102010026781 A1 | 1/2012 |

*Primary Examiner* — Mandrita Brahmachari
(74) *Attorney, Agent, or Firm* — Anglehart et al.

(57) ABSTRACT

The system and method disclosed collects user reported, self-monitored On-task/Off-task Behavior, Fidgeting Behaviors and Walking/Running behaviors as quantified by motion sensors and an intelligent scheduling system. The collected data tells the reminder device what environment a user is scheduled to be in at any point in time in order to appropriately collect behavioral information and use said information to encourage users to be mindful of their own actions and behaviors in order to increase time spent on-task.

23 Claims, 4 Drawing Sheets

(56) References Cited

U.S. PATENT DOCUMENTS

| | | | |
|---|---|---|---|
| 2014/0245789 A1* | 9/2014 | Proud | A44C 5/0015 |
| | | | 63/1.13 |
| 2014/0370471 A1 | 12/2014 | Brancaccio | |
| 2015/0288797 A1 | 10/2015 | Vincent | |
| 2016/0082222 A1* | 3/2016 | Garcia Molina | A61B 5/4815 |
| | | | 600/27 |
| 2016/0161985 A1* | 6/2016 | Zhang | G06F 1/163 |
| | | | 361/679.03 |
| 2016/0287166 A1 | 10/2016 | Tran | |
| 2016/0310341 A1* | 10/2016 | Yu | A61B 5/7445 |
| 2017/0228121 A1* | 8/2017 | Wosk | G06F 3/0487 |
| 2017/0293727 A1 | 10/2017 | Klaassen et al. | |
| 2018/0188694 A1* | 7/2018 | Wu | G04G 99/006 |

* cited by examiner

APPARATUS AND METHOD FOR A PERSONALIZED REMINDER WITH INTELLIGENT SELF-MONITORING

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

BACKGROUND

Wearable systems that incorporate sensors to determine physical parameters of a wearer are known and present in the marketplace. Sensors indicating position, heartrate, movement in exercise positions, among other parameters collect data about the user and provide feedback to a user in realtime. Such systems may also be connected through a data communications channel to a computer system having analytical software to review collected data and provide analysis to a user or third party on parameters that are of interest to the user. With appropriately miniaturized electronics, the sensors may be located in a smaller portion of the user's body such as the ear. The data collected may be used to assist users understanding about their physical state during exercise, work, sleep, or other activities.

Feedback may also be provided to the user through a wearable device. The feedback may be through elements installed within the wearable device or may be sent to a mobile or wifi connected device that is in data communication with the wearable device. The feedback may form a portion of a user's medical record, or may be used to assist the wearer in keeping physical parameters within certain specified ranges during physical activity.

The wearable device may also be active to determine whether a user was engaged in undesirable behavior while the device is being worn. The wearable device may actively monitor the user to collect and store information about the user's activities at certain time periods and/or when the user's activity level exceeds pre-configured thresholds for specified activities. If the determined intensity of activity exceeds the established threshold, the device could activate the feedback mechanism in an attempt to provide correction for the user to follow so as to change the user's behavior. However, currently available wearable devices do not often provide the user with the capability to interact with the feedback capability of the wearable device to provide customized feedback and corrective capability.

BRIEF DESCRIPTION OF THE DRAWINGS

Certain illustrative embodiments illustrating organization and method of operation, together with objects and advantages may be best understood by reference to the detailed description that follows taken in conjunction with the accompanying drawings in which.

DETAILED DESCRIPTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

Reference throughout this document to "On-task Behavior", or similar terms "Focused Behavior", "Focus", or "Attention" refers to any behaviors deemed appropriate or desired by the user in the context of using a reminder device. In a non-limiting example, if a user desires to demonstrate better attention, listening skills or work completion, these behaviors may be deemed as "On-Task Behavior".

Reference throughout this document to "Off-task Behavior" refers to behaviors deemed inappropriate or not desired by the user in the context of using a reminder device.

Reference throughout this document to "Fidgeting", refers to how frequently an individual tends to shuffle, wiggle or engage in other 'still or seated movements', including but not limited to wrist and hand movements, and including hand flapping, hand-wringing and other stereotyped behaviors commonly associated with Autism stimming, that may affect the person's productive behavior and/or be related to their ability to quietly sit or stand and attend or focus on a given task.

In an embodiment with regard to these reported behaviors, users of the invention described in this document may utilize a well-known technique called Self-Monitoring, or SM. Self-Monitoring is a well-documented, highly researched behavioral intervention which has been shown to be a highly effective means of increasing desired behaviors and decreasing undesired behaviors. Previously, however, there has been a lack of integration between SM and technology. This document presents a system and method to operatively utilize SM to improve the on-task behavior, focus and/or attention of a user by precisely adjusting factors that adjust the frequency, intensity and patterning of reminder prompts through various stimuli, such as a tactile vibration, audible tone, visual stimulus, or other stimuli that may form a reminder prompt, defined as, in a non-limiting example, "F-factors".

In this embodiment, the system and method utilizes a pool of research-based data tables to pseudorandomize meta-cognitive reminders. Such reminders encourage users to be more cognizant and aware of their own behaviors. This self-awareness of personal behaviors may in-turn help increase an individual's ability to stay on-task. By providing a platform to query a user regarding their own on-task and off-task behaviors, as well as to collect and compile in order to intelligently harness this data, the system and method described may be able to impart change through targeted reminders driven by actual, longitudinal user data.

In an embodiment, an algorithm may determine when and how to adjust reminders based-on user input in regards to self-reported on-task and off-task behaviors. Over time, this system progressively gathers user data and learns details of a user's activity and habits, and becomes more and more attuned to the user's needs. The device containing the sensors and that provides prompt reminders to a user, is worn by the user. In a non-limiting example, the device may sample the user's behavior multiple times per second, collecting measurements from each sampling period, and provide a prompt to the user when the system determines that any change that merits a reminder to the user has occurred. Based-on collected data that illumine user behaviors, a computer software module may be operative to determine the most appropriate minimum and maximum values for prompt timing to ensure maximum on-task behavior, while also minimizing over-prompting to keep meaningfulness high and habituation low.

In an embodiment, while collecting data, it is imperative to categorize the collected information into useful segments. If not properly categorized, the data becomes irrelevant due to situational constraints. In a non-limiting example, if an individual desires to actively track the ability to listen to a teacher or lesson, but from time to time is sitting at a cafeteria table during lunch instead of being engaged in listening to a teacher or lesson, then the information collected is not relevant. Even different environments that are more relevant tend to net differing levels of interest, attention and on/off-task behaviors. For this reason, a scheduling component is incorporated into the system and method to intelligently collect and organize data. In a non-limiting example, data will not be collected during certain, predetermined periods of time, such as during lunch, physical education, or other time periods in which the user may be distracted or not dedicated to a desired task, but may be collected and then leveraged in a unique fashion during other time periods. In a non-limiting example, reminders may also be amplified, as needed, in certain key environments. To do this, a calendar or schedule is initially completed by the user, including start and end times to provide the system with insight into a user's established schedule. The reminder device component of the system includes a real-time clock feature which auto-updates in order to correctly utilize schedule events and engage reminders.

In an embodiment, the system and method may actively collect a user's reported behaviors in order to continually optimize each of several focus factors, previously defined as "F factors". Based on a user's reported behaviors to a posed question, such as "When you feel this vibrate, ask yourself if you were on-task or off-task—press user response button 2 times for on-task and 1 time for off-task", a computer algorithm is operative to determine whether or not to increase, decrease or leave unchanged the aforementioned factors in order to continually provide as much prompting as necessary to improve users on-task behaviors, but as little prompting to as not become burdensome or to force user to habituate. Habituation is further staved-off by pseudo-randomizing one or more of the F factors.

In an exemplary embodiment, the system and method described comprises a device, preferably worn on the wrist although this should in no way be considered limiting as the device may be worn on any appendage or as a necklace, headband, or other fashion-conscious garment. The device may have a processor that incorporates a machine learning algorithm to determine alternations in vibrations and changes in the pitch of generated tones to provide reminders to a wearer to remain focused on an activity. In this exemplary embodiment, the machine learning algorithm is operative to determine the best times to remind the wearer based upon user action in response to the user history of responses to reminder prompts. The machine learning algorithm may also take into account the user's daily or weekly schedule of activities and tasks in determining when to send a reminder prompt. The wearer's schedule may be added to provide more directed collection of data with regard to on/off task time percentage, goals of the user, and sending an automatic email report on user activity to a caregiver, parent, health care professional, or other authority associated with the user.

In an alternative exemplary embodiment, a wearer, in some instances a child, may receive additional mandatory remind times when they must respond to a device vibration and/or tone by tapping the device. Device vibrations may indicate states or timing through alternative vibrations, tones, or other distinguishing tactile or audible actions. The machine learning algorithm associated with the device may modify vibrations, tones, sequences, intensity and other prompt actions based upon user response. The vibrations and frequencies of the tones may change based upon patterns of response from the user, thus learning the habits of the user in terms of response to prompts.

In an embodiment, the device may be in communication with a system server for reporting, updates, and other communications.

In additional embodiments, the device may track stationary movement (fidgeting, etc.) to quantify the user's seated behavior. Tracking fidgeting behavior permits the system and method to perform updates and changes to the prompt generation algorithm based upon physical response or reaction time, as well as to situations in which the user does not respond to a prompt. In additional embodiments, the system and method may modify the prompt generation algorithm based upon a user's class scheduling, if the user is a student, or based upon the previous week's performance on responses to prompts transmitting to the device for action by the user.

In an embodiment, the system also utilizes trends in individual user's behaviors to prescribe suggestions, by combining research-based interventions with actual user behaviors measured over time to drive the application, duration and intensity of said research-based behavioral interventions. This allows information to be presented to teachers, supervisors, other authority figures, or the users themselves with individualized recommendations for each user in each environment such as classes, job functions, or any other environment in which performance is expected and required.

Walking/Running/Fidgeting are also quantified by advanced motion sensors and tracked over time in order to determine how active an individual may be, whether or not their activity level is considered 'over-active' relative to both self and peers. The determination of activity level based upon these activities may then prompt an increase in the frequency of reminders, as necessary, based-on excessive levels of fidgeting to remind users to re-engage in their desired on-task behaviors.

The system implements all data collected (Self-Monitored responses, physical motions, schedule and environment) to make real-time on-the-fly changes to reminder prompt durations, frequency, amplitude and wavelength to both custom-tailor to users exact needs, so as not to over, or under, prompt, as well to provide a constantly unique prompt experience, which may help increase time on-task and reduce habituation.

Figure 1:
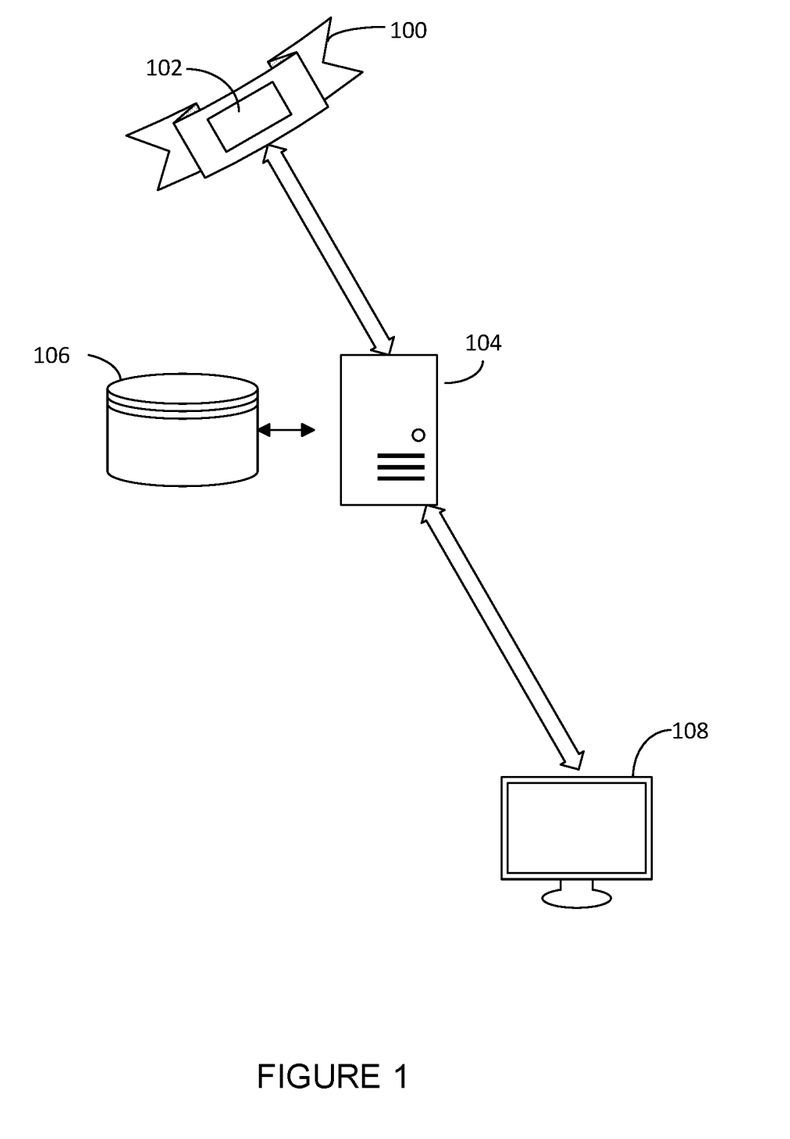
FIG. 1 is a view of a system configuration consistent with certain embodiments of the present invention.

Turning now to FIG. 1, this figure presents a view of a system configuration consistent with certain embodiments of the present invention. In an exemplary embodiment, the system and method comprises a device 100 that is worn by a user. One or more sensors, including but not limited to motion sensors, may be incorporated into the device to collect motion data associated with the user. One or more prompt elements, including, but not limited to, elements that produce tactile, visual, auditory, or other prompts to catch the attention of the user are also included in the device 100. The device 100 may also incorporate a display element 102 that provides for visual information to be presented to the user at the determination of the system. The device 100 may also contain an RF, Wifi, Bluetooth, Bluetooth Low Energy (BLE), or other transmission protocols developed and released for use in wired or wireless data communication.

In an embodiment, the transmission capability may provide for connection and communication with a system server 104. The system server 104 may incorporate a plurality of software modules (not shown) operative to transmit commands and data to the device 100 and receive data from the device 100. The software modules may transmit prompt commands to the device 100, stimulating any of the tactile, visual, auditory, or other prompt elements to activate and provide a prompt to capture the user's attention. The user will sense the prompt and provide a response to the prompt by tapping or otherwise interacting with the device 100 to indicate whether the user is on-task or off-task at the time the prompt was noticed by the user. The response by the user may then be transmitted by the device 100 back to the server 104 where the user response may be stored in a database element 106 in a file dedicated to the user and containing all response and tracking data associated with each user. The server 104 may then communicate a report to a display or other interactive device 108 associated with a parent, teacher, healthcare professional, or other authority figure associated with the user. This informative report can be used to both inform as well as motivate the user by providing customized reporting on progress towards behavioral improvement, personalized goals or peer-based benchmarks; this can be presented to the user in the form of a customized report, animation/cartoon character, avatar or other modality. Progress from successful feedback to SM prompts may also be used to generate 'points', tokens, credits or the like in order to motivate the user by allowing them additional time, features, etc. for an in-application game, or a game external from the device application. The device and companion software can also utilize data garnered from the device to drive individualized recommendations, suggestions, and/or feedback, presented in a daily, weekly or monthly report.

Figure 2:
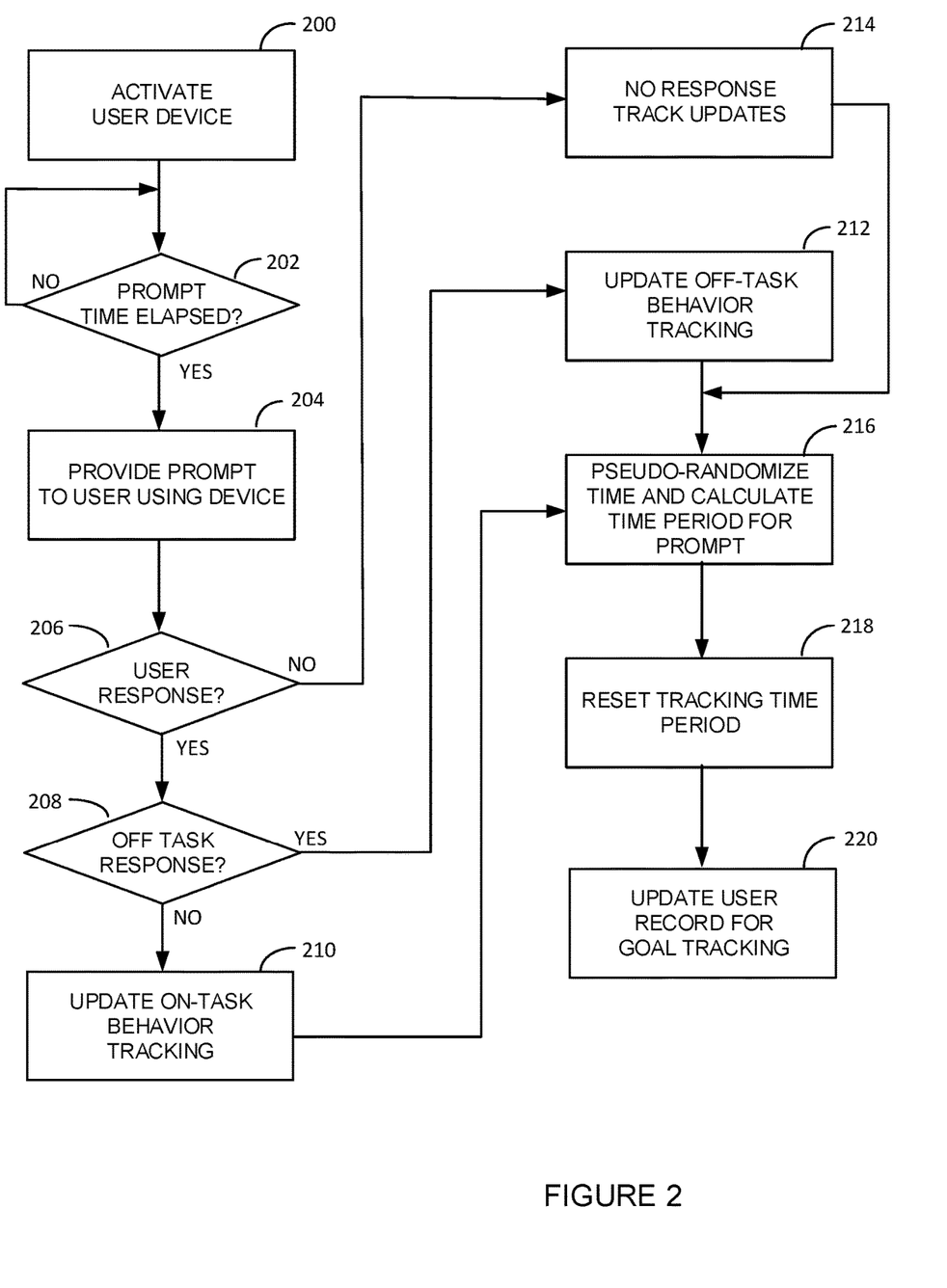
FIG. 2 is an operational flow diagram for pseudo-randomized operation consistent with certain embodiments of the present invention.

Turning now to FIG. 2, this figure presents an operational flow diagram for pseudo-randomized operation consistent with certain embodiments of the present invention. In an exemplary embodiment, the user attaches the device to their person and the system is activated by the user at 200. The device interrogates the internal prompt timing value transmitted from the server to the device at 202 and checks to determine if the prompt timing value has been exceeded.

At 204 the device has determined that the prompt timing value has been exceeded and initiates the prompt chosen by the user, whether tactile, auditory, visual, or other prompt indication. At 206 the device waits a pre-configured amount of time for a response to the prompt indication from the user. If the device receives a response from the user in the pre-configured amount of time permitted for the user to respond, at 208 the device reviews the response from the user to determine if the user is indicating they are on-task or off-task. If the user has indicated by the appropriate response that they were on-task at the time they received the prompt from the device, the device at 210 sends an indication of on-task behavior to the system server which is then active to update the user on-task tracking file in the database. If, however, the user has indicated, again by the appropriate response, that they were off task, the device at 212 sends an indication of off-task behavior to the system server which is then active to update the user off-task tracking file in the database.

At 214, when the user has not provided a response to the prompt transmitted by the device, the device sends an indication of a lack of response to the prompt to the system server which is then active to update the user no-response tracking file in the database.

Regardless of the response or lack of response to the prompt by the user, at 216 the system server is operable to create a new time period setting for the next prompt interval to be used by the device by activating a pseudo-randomization algorithm to calculate a new prompt time period utilizing tracked on and off task time percentage and the user's goals. At 218, the system server resets the prompt time period in the internal database and transmits this new time period value to the device. The device replaces the previous prompt time interval with the newly received prompt time interval and begins checking for elapsed time against the prompt time interval. At 220 the system updates the user record for goal tracking based upon the user response information.

Figure 3:
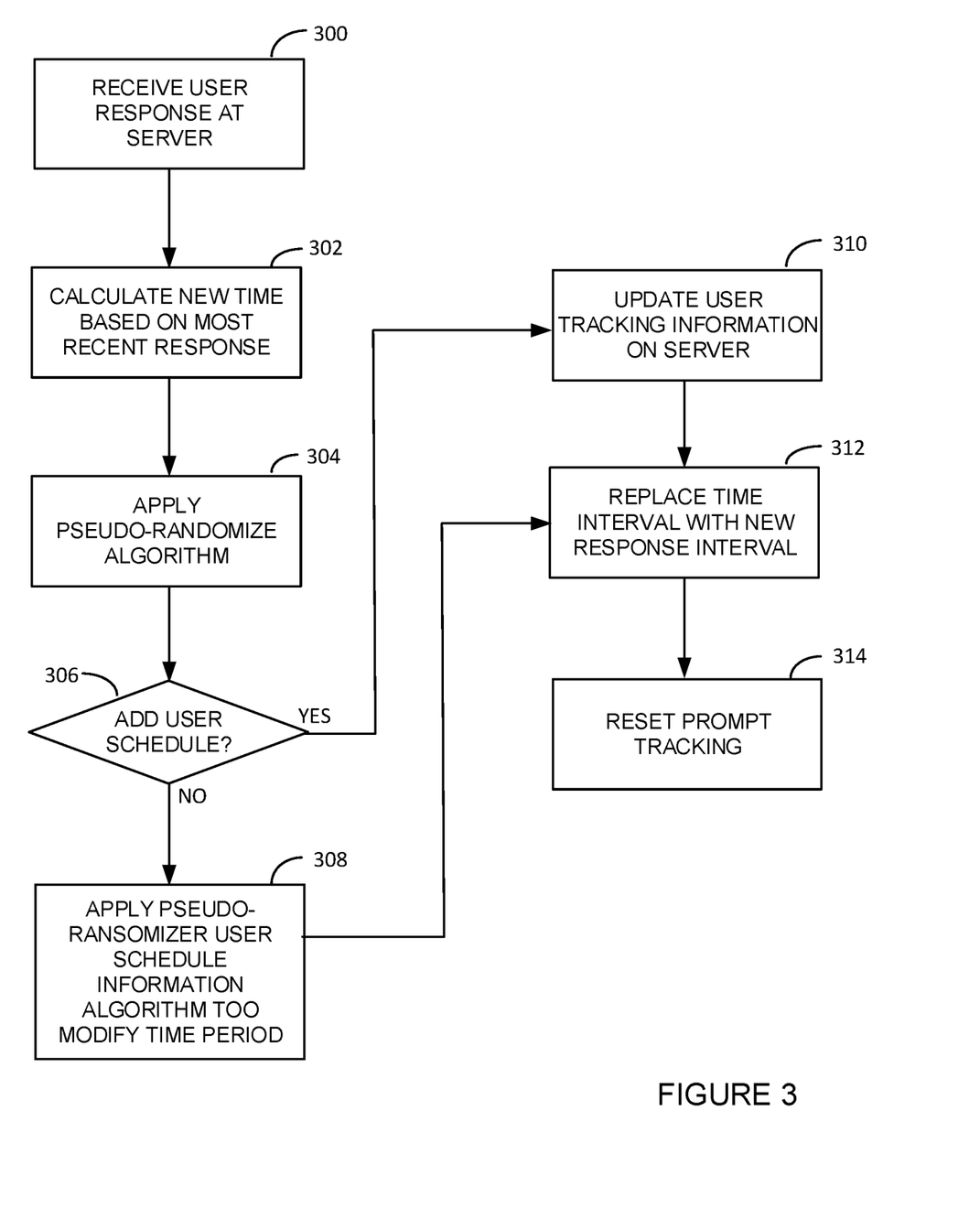
FIG. 3 is an operational flow diagram for prompts incorporated a user's schedule consistent with certain embodiments of the present invention.

Turning now to FIG. 3, this figure presents an operational flow diagram for prompts incorporated a user's schedule consistent with certain embodiments of the present invention. In an exemplary embodiment, at 300 the system server may receive a response from the device associated with a user. At 302 the system server tracking software module may be operable to calculate the time from the most recent response received from the user associated with the device. At 304, the system server is operable to create a new time period setting for the next prompt interval to be used by the device by activating a pseudo-randomization algorithm to calculate a new prompt time period utilizing on and off task time percentage and the user's goals. At 306, the system server determines whether the user's schedule is to be utilized in the calculation of a new prompt time period. If the user's schedule is to be utilized, at 308 the system server may take into account the user's schedule, special circumstances, previous response performance, and input these parameters into the pseudo-randomizer software module. The pseudo-randomizer module may then utilize these input parameters and initiate the pseudo-randomization algorithm to modify the response time period by determining the most appropriate minimum and maximum values for prompt timing to ensure maximum on-task behavior, while also minimizing over-prompting to keep meaningfulness high and habituation low. The new prompt time period calculated utilizing the user's schedule is used to update the user tracking information on the system server.

If the user's schedule is not to be used in the calculation of a new prompt time period, the system server simply updates the user tracking information with the new prompt time period that was calculated without input from the user's schedule at 310. At 312, the system server replaces the elapsed prompt time period with the newly calculated prompt time period and transmits the newly calculated prompt time period to the device to replace the prompt time period just elapsed. The system server then updates the database with all tracking information and resets the tracking information for the user.

Figure 4:
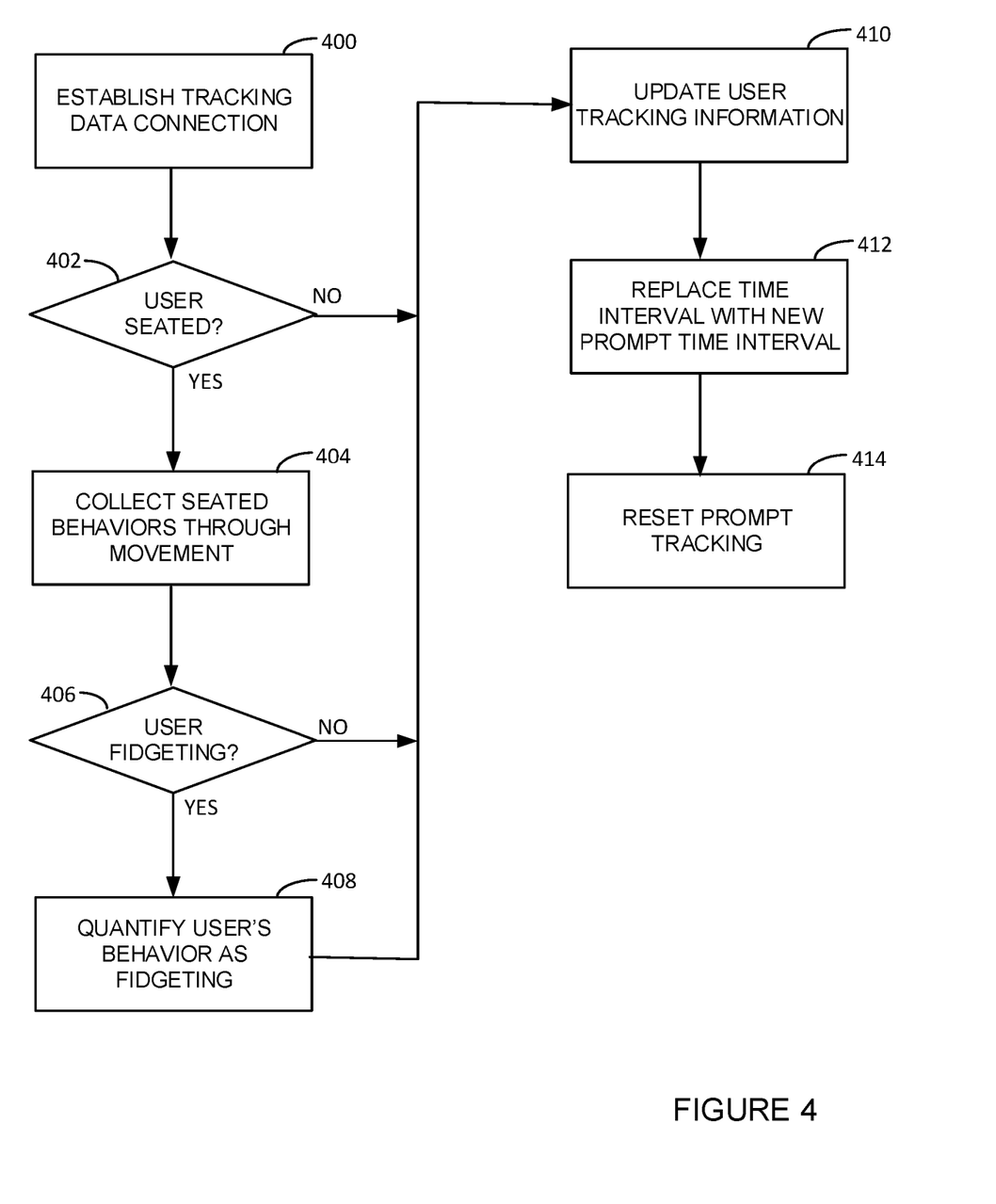
FIG. 4 is an operational flow diagram for detecting fidget behavior consistent with certain embodiments of the present invention.

Turning now to FIG. 4, this figure presents an operational flow diagram for detecting fidget behavior consistent with certain embodiments of the present invention. In this exemplary embodiment, the tracking information input by the user may be stored within the wearable device. The system server establishes a data communication connection with the device to establish a tracking connection between the device associated with a user and the system server at 400. The system server may transmit any tracking information stored within the server to a cloud-based storage facility, collect tracking information from the wearable device and transmit the collected tracking information to the cloud-based storage, or provide a real-time update of tracking information from the wearable device, through the server, and on to the cloud-based storage facility. The system server at 402 is active to determine that the user is seated by receiving and analyzing motion sensor data to determine the user's movement. If the user's movement is constrained to within a certain parameter set that indicates the user is not moving to a different physical position, not walking or running, the system server may determine that the user is seated. In an alternative embodiment, the system server at 402 may also be active to determine that a user is standing, hopping, or remaining in one spot for a period of time but performing fidgeting-type behaviors.

In an embodiment, the system is active to collect all data associated with a user, regardless of physical position, whether standing, seated, reclining, or in active motion. However, if the user is determined to be seated or remaining substantially in a single physical position by sensor data analysis, at 404 the system server is active to categorize collected data as associated with a localized physical position, either seated or standing, and collects all sensor data from the device as indicia of a user's fidgeting behaviors. At 406, the movement software module is operative to determine if the seated behaviors of a user are indicative of fidgeting, as defined previously. If the behaviors indicate that the user is fidgeting at 408 the system server quantifies the user's movement as fidgeting and stores the sensor data along with an indication of fidgeting behavior and timing data associated with the length of time the user is exhibiting this fidgeting behavior. Whether the user's behavior is indicative of fidgeting or not, the system server updates the tracking information associated with the user at 410. At 412, the system server calculates a new prompt time interval through a pseudo-randomization algorithm with an added parameter to account for fidgeting behavior and transmits the newly calculated prompt time interval to the device associated with the user. At 414, the system is operative to reset the prompt interval tracking to continue operation.

While certain illustrative embodiments have been described, it is evident that many alternatives, modifications, permutations and variations will become apparent to those skilled in the art in light of the foregoing description.

We claim:

1. A wearable device to modify behavior of a user, the device comprising:
 a processor;
 a wireless data communication interface operably coupled to the processor; and
 memory operably coupled to the processor, the memory storing instructions which when executed by the processor cause the processor to perform a method comprising:
  producing, when an elapsed time interval reaches a first prompt timing value, a stimulatory prompt to a user;
  waiting for up to a preconfigured amount of time to receive a response by the user to the stimulatory prompt, the response being determined by the user through self-monitoring of behavior of the user at a time of responding to the stimulatory prompt, the response being received via a first or a second defined user interaction with the device, wherein:
   (i) the first defined user interaction with the device is performed by the user to indicate that the user is engaged in behavior determined by the user to be on-task behavior, and
   (ii) the second defined user interaction with the device is performed by the user to indicate that the user is engaged in behavior determined by the user to be off-task behavior,
  providing, when the response to the stimulatory prompt has been received or the preconfigured amount of time has elapsed without user response, an indication of the response or lack of response, wherein the processor is operable to provide:
   (i) a first type of indication when the response is received via the first defined user interaction with the device,
   (ii) a second type of indication when the response was received via the second defined user interaction with the device, and
   (iii) a third type of indication when a response is not received in the preconfigured amount of time;
  determining a second prompt timing value based at least in part on the type of indication resulting from said providing of the indication of the response or the lack of response; and
  producing, when a further elapsed time interval reaches the second prompt timing value, a further stimulatory prompt to the user.

2. The device of claim 1, wherein:
 the on-task behavior, as determined by the user, comprises behaviors deemed by the user to be appropriate or desirable in the context of using the wearable device, and
 the off-task behavior, as determined by the user, comprises behaviors deemed by the user to be inappropriate or undesirable in the context of using the wearable device.

3. The device of claim 1, wherein the determining of the second prompt timing value is based at least in part on one or more of:

a relative number of responses of the first type of indication, indicating that the user is engaged in on-task behavior, a relative number of responses of the second type of indication, indicating that the user is engaged in off-task behavior, and a relative number of the third type of indication, indicating a lack of response.

4. The device of claim 1, wherein the determining of the second prompt timing value comprises using a pseudo-randomization algorithm to reduce user habituation.

5. The device of claim 1, wherein the determining of the second prompt timing value is based at least in part on a real-time clock and a schedule of the user defining time periods of academic subjects and/or activities.

6. The device of claim 1, wherein the determining of the second prompt timing value is based at least in part on a real-time clock and a machine learning algorithm which has been trained using data relating to a schedule of the user defining time periods of academic subjects and/or activities.

7. The device of claim 1, wherein the memory stores instructions which when executed by the processor cause the processor to perform the method further comprising:

adjusting characteristics of the stimulatory prompt based at least in part on the type of indication resulting from said providing of the indication of the response or the lack of response, wherein the characteristics of the stimulatory prompt to be adjusted include one or more of: frequency, wavelength, intensity, amplitude, and pattern.

8. The device of claim 1, wherein the determining of the second prompt timing value comprises a calculation performed by a server, and the memory stores instructions which when executed by the processor cause the processor to perform the method further comprising:

receiving, via the wireless data communication interface of the device, the second prompt timing value from the server.

9. The device of claim 1, wherein the determining of the second prompt timing value is based at least in part on a machine learning algorithm which has been trained using historical data relating to the type of indication resulting from said providing of the indication of the response or the lack of response.

10. The device of claim 1, further comprising at least one position sensor, wherein the memory stores instructions which when executed by the processor cause the processor to perform the method further comprising:

periodically measuring movement of the user, using the at least one position sensor, to produce data indicative of movement of the user; and analyzing the data indicative of movement of the user to detect fidgeting-type behaviors by the user.

11. The device of claim 10, wherein the analyzing of the data indicative of the movement of the user to detect fidgeting-type behaviors comprises determining whether the movement of the user is constrained to within a defined parameter set indicating that the user is remaining in a specific physical location.

12. The device of claim 10, wherein the determining of the second prompt timing value is based at least in part on the analyzing of the data indicative of the movement of the user to detect fidgeting-type behaviors.

13. A system to modify behavior of a user, the system comprising:

at least one server comprising a processor, memory operably coupled to the processor, and a wireless data communication interface operably coupled to the processor, the wireless data communication interface adapted to communicate with one or more wearable devices, the memory storing instructions which when executed by the processor cause the processor to perform a method comprising:

transmitting, via the wireless data communication interface to a selected one of the one or more wearable devices, a first prompt timing value to initiate, when an elapsed time interval reaches the first prompt timing value, a stimulatory prompt to a user produced by the selected wearable device;

receiving from the selected wearable device an indication of the response or lack of response by the user to the stimulatory prompt, the response being determined by the user through self-monitoring of behavior of the user at a time of responding to the stimulatory prompt, the response being received via a first or a second defined user interaction with the device, wherein:

(i) the first defined user interaction with the device is performed by the user to indicate that the user is engaged in behavior determined by the user to be on-task behavior, and (ii) the second defined user interaction with the device is performed by the user to indicate that the user is engaged in behavior determined by the user to be off-task behavior, and wherein the indication of the response or lack of response by the user to the stimulatory prompt is provided by the selected wearable device when the response to the stimulatory prompt has been received by the selected wearable device or the preconfigured amount of time has elapsed without user response, wherein the selected wearable device is operable to provide:

(i) a first type of indication when the response is received via the first defined user interaction with the device, (ii) a second type of indication when the response was received via the second defined user interaction with the device, and (iii) a third type of indication when a response is not received in the preconfigured amount of time;

determining a second prompt timing value based at least in part on the type of indication resulting from said receiving from the selected wearable device an indication of the response or lack of response by the user to the stimulatory prompt; and transmitting, via the wireless data communication interface to the selected device, the second prompt timing value to initiate, when a further elapsed time interval reaches the second prompt timing value, a further stimulatory prompt produced by the device.

14. The system of claim 13, wherein:

the on-task behavior, as determined by the user, comprises behaviors deemed by the user to be appropriate or desirable in the context of using the wearable device, and the off-task behavior, as determined by the user, comprises behaviors deemed by the user to be inappropriate or undesirable in the context of using the wearable device.

15. The system of claim 13, wherein the determining of the second prompt timing value is based at least in part on one or more of:

a relative number of responses of the first type of indication, indicating that the user is engaged in on-task behavior, a relative number of responses of the second type of indication, indicating that the user is engaged in off-task behavior, and a relative number of the third type of indication, indicating a lack of response.

16. The system of claim 13, wherein the determining of the second prompt timing value comprises using a pseudo-randomization algorithm to reduce user habituation.

17. The system of claim 13, wherein the determining of the second prompt timing value is based at least in part on a real-time clock and a schedule of the user defining time periods of academic subjects and/or activities.

18. The system of claim 13, wherein the determining of the second prompt timing value is based at least in part on a real-time clock and a machine learning algorithm which has been trained using data relating to a schedule of the user defining time periods of academic subjects and/or activities.

19. The system of claim 13, wherein the memory stores instructions which when executed by the processor cause the processor to perform the method further comprising:

adjusting characteristics of the stimulatory prompt based at least in part on the type of indication resulting from said providing of the indication of the response or the lack of response, wherein the characteristics of the stimulatory prompt to be adjusted include one or more of: frequency, wavelength, intensity, amplitude, and pattern.

20. The system of claim 13, wherein the determining of the second prompt timing value is based at least in part on a machine learning algorithm which has been trained using historical data relating to the type of indication resulting from said providing of the indication of the response or the lack of response.

21. The system of claim 13, wherein the memory stores instructions which when executed by the processor cause the processor to perform the method further comprising:

receiving, from the selected wearable device, data indicative of movement of the user; and analyzing the data indicative of movement of the user to detect fidgeting-type behaviors by the user.

22. The system of claim 21, wherein the analyzing of the data indicative of the movement of the user to detect fidgeting-type behaviors comprises determining whether the movement of the user is constrained to within a defined parameter set indicating that the user is remaining in a specific physical location.

23. The system of claim 22, wherein the determining of the second prompt timing value is based at least in part on the analyzing of the data indicative of the movement of the user to detect fidgeting-type behaviors.

* * * * *